US006831100B2

(12) United States Patent
Khanuja et al.

(10) Patent No.: US 6,831,100 B2
(45) Date of Patent: Dec. 14, 2004

(54) MENTHYL BENZOATE FORMULATIONS FOR EXTERNAL UV PROTECTION

(75) Inventors: Suman Preet Singh Khanuja, Lucknow (IN); Krishna Kumar Agarwal, Lucknow (IN); Tiruppadiripuliyur Ranganathan Santha Kumar, Lucknow (IN); Atique Ahmad, Lucknow (IN); Ajit Kumar Shasany, Lucknow (IN); Mahendra Pandurang Darokar, Lucknow (IN); Sushil Kumar, Lucknow (IN)

(73) Assignee: Council of Scientific & Industrial Research Rafi Marg, New Delhi (IN)

( * ) Notice: Subject to any disclaimer, the term of this patent is extended or adjusted under 35 U.S.C. 154(b) by 0 days.

(21) Appl. No.: 10/462,646

(22) Filed: Jun. 17, 2003

(65) Prior Publication Data

US 2003/0215901 A1 Nov. 20, 2003

Related U.S. Application Data

(62) Division of application No. 09/537,716, filed on Mar. 30, 2000, now abandoned.

(51) Int. Cl.$^7$ .................................... A61K 31/21
(52) U.S. Cl. .................................... 514/506
(58) Field of Search .................................... 514/506

(56) References Cited

FOREIGN PATENT DOCUMENTS

RO 109503 * 3/1995

OTHER PUBLICATIONS

Henderson et al., Mutagenesis 1994 Sep:9(5):459–65.
Kumar, "Properties of Adenyl Cyclase and Cyclic Adenosine 3',5'–Monophosphate Receptor Protein–Deficient Mutants of *Escherichia coli*", pp. 545–554, Feb. 1976, Journal of Bacteriology, vol. 125, No. 2.
Sambuco et al., J. Am. Academy Dermatology (1984) I 737–43.
Biotechnology Culture Media.

* cited by examiner

*Primary Examiner*—Jean C. Witz
(74) *Attorney, Agent, or Firm*—Donald R. Studebaker; Nixon Peabody, LLP

(57) ABSTRACT

The present invention describes a novel and very quick bacterial system based screening protocol to detect UV protectant molecules and determining their efficacy for the extent of protection against Ultraviolet radiation in biological systems, identifying a new use of the compound menthyl benzoate as efficient UV protectant suitable for providing protection against the harmful effects of ultraviolet radiation and the extent of protection provided by menthyl benzoate.

6 Claims, No Drawings

MENTHYL BENZOATE FORMULATIONS FOR EXTERNAL UV PROTECTION

This application is a division of application Ser. No. 09/537,716 filed Mar. 30, 2000, now abandoned.

FIELD OF INVENTION

The present invention relates to the development and use of a novel bacterial system based protocol to screen the efficacy of the chemical compounds for Ultraviolet radiation protection. Preferably, the invention relates to a new use of the compound menthyl benzoate suitable for providing protection against the harmful effects of ultraviolet radiation. The invention also extends to identifying the quantum of protection provided by menthyl benzoate, which is much higher than the known UV protectants like dibenzoyl methane and benzyl benzoate.

BACKGROUND OF THE INVENTION

The exposure to sunlight can pose a variety of damages to the skin and the damaging effects may result in hazardous effects like sunburn which primarily result from exposure to UVB radiation within the sunlight spectrum having a wavelength of about 290 to 320 nm. But continuous exposure over the long run may also lead to malignant cancerous cells on the skin surface. Studies have demonstrated a strong relationship between sunlight exposure and human skin cancer. Other hazards of ultra violet radiation exposure include premature aging of the skin, which is primarily caused by the UVA radiation having a wavelength of from about 320 nm to about 400 nm. This condition is characterized by wrinkling and pigments changes of the skin, along with other physical changes such as cracking, telangiectasis, solar dermatoses, ecchymoses, and loss of elasticity etc.

Due to the rising incidence and awareness about the hazards of sun exposure with the realization of ozone layer depletion due to green house gases in the atmosphere, many compounds and compositions have been appearing in the market and the prior arts are full of such compositions for cosmetic and personal care products. But most of the sunscreen products, in particular do not provide sufficient protection against broad spectrum UV radiations, i.e., protection against both UVB and UVA wavelength ranges. Mostly the commercially available sunscreen products absorb UV radiation in the wavelengt range of 290 nm to 320 nm (UVB domain) protecting against the sunburn. Their ineffectiveness in the 320 nm to 400 range (UVA domain) leaves the skin vulnerable to premature aging and wrinkling. General lack of UVA absorbing sunscreen actives or UV sieve compounds is conspicuous among the products, which are both commercially available and also approved for global use.

One class of the available sunscreen actives includes dibenzoylmethane compounds which provide broad-spectrum UV protection such as 4-tert-butyl-4'-methoxydibenzoylmethane. Unfortunately, these sunscreens tend to photodegrade upon exposure to UV radiation thereby reducing their UVA efficacy. Consequently, sunscreen products, which include these compounds, are typically difficult to formulate due to the inherent lack of photostability of dibenzoylmethane compounds. Further, modification of these chemicals may be hazardous to the skin or make them environmentally unsafe. From plant sources, the compounds known to be safe for human use can be screened isolated and modified for use as sunscreen. Sunlight is required for health, and a sunscreen composition absorbing 100% of the sunlight is not desirable. The desirable feature is that the damaging wavelength range of sunlight spectrum should be reduced to the safe threshold level which is skin and tissue safe by using the compounds which are harmless to the biological system.

Thus, there is a need for screening compounds from diverse sources, which can be used in compositions suitable for providing protection against the harmful effects of UV radiation to human skin. In particular, in the personal care products industry, there is a rising need for sunscreen products possessing excellent photostability, efficiency with the capability to provide broad-spectrum UV protection (i.e., against both UVA and UVB radiation) in a safe and economical manner.

With these rationale in mind the applicants constructed a bacterial model system and a method to use the system in rapid large scale screening of compounds which can protect the cells against UV damage (312 nm to 365nm) either in form of a sieve or in vicinity of target cells. A variety of compounds including several monoterpenes and their derivatives were screened using the known protectant Benzyl benzoate and Dibenzoyl methane as control molecules. The procedure is rapid, novel, most convenient and environmentally compatible not requiring human or animal subject and/or complexities of cell culture in skin testing. Results can be obtained overnight and are 100% interpretable as evident from the control compounds and additionally provide quantifiable data on extent of protection. In this screening approach which itself was the objective of the invention menthyl benzoate was found to provide significant protection with excellent efficiency for both UV radiation (UVA and UVB) and hence, making its use as UV protectant evident.

OBJECTS OF THE INVENTION

The main object of the invention relates to a new alternative and quick protocol to screen large number of compounds for UV protection. This was achieved by testing the known UV protectants as well as a known compound not formerly for UV protection.

Another object of the invention relates to providing a compound which can be used for protecting biological systems from UV light.

Yet another object of the invention relates to providing a biologically safe compound which can be used as a UV protectant for biological systems.

DETAILED DESCRIPTION OF THE INVENTION

The invention provides a method for screening compounds for effective protection against the harmful ultraviolet radiation, thereby providing UV screen to prevent the harmful affect of the radiation on the biological system which comprises, a. Inoculating a single colony in 5 ml Luria broth and incubating the broth at 37° C. temperature for at least 16 hours in a water bath shaker and is growing in presence of test compounds with plain LB as growth medium, b. harvesting the bacterial culture by centrifugation and suspending the pellet in an equal amount of sterile distilled water, c. transferring at least 0.3 ml of the broth culture of the bacteria to petriplates so as to form a thin layer at the bottom of the plates (in replicates), d. optionally covering the plates with UV transparent film, which is coated with different concentrations of the test compounds, e. placing a UV source at least 10 cm above the plates (which may vary depending upon the experiment), f. switching on the light source for different time intervals for the predetermined lethality levels based on the control bacteria determined by UV exposure through uncoated film, g. determining the viable cfu (colony forming unit) count by serially diluting the exposed and control bacteria, plating the bacteria on the Luria agar plates, then counting the viable units of the bacteria forming colonies.

h. comparing the colony forming units of UV exposed bacterial cultures through coated and uncoated film to compute the protection percentages for different compounds.

i. calculating the killing percentage by comparing the cfu (colony forming unit) count of UV exposed and control bacteria.

In an embodiment the bacteria used in the method of the present invention may be *Escherichia coil* or any other strains, species or genus which shows substantial sensitivity to UV light exposures in terms of killing.

In another embodiment of the present invention, the UV radiation may range between 290 to 400 nm.

In yet another embodiment of the present invention provided is a novel use of a semi-synthetic compound menthyl benzoate which can be used as an UV protectant filter providing better protection, by screening the ultra violet rays, thereby providing protection to the biological systems, including human skin.

In yet another embodiment of the present invention provided is a formulation comprising menthyl benzoate ranging between 0.002–0.02% (w/w) in glycerin, cold cream, skin cream, antibiotic ointments, sunscreen lotions and any other body care compositions used for external UV protection applications.

The following experiments shown as examples of the invention were critically performed to develop a novel and very quick bacterial system based screening protocol to detect UV protectant molecules and determining their efficacy for the extent of protection against Ultraviolet radiation in biological systems. The invention further could lead to the finding of a new use of the compound menthyl benzoate as efficient UV protectant and the compositions containing the compound, suitable for providing protection against the harmful effects of ultraviolet radiation. The extent of protection by menthyl benzoate is much higher than the known UV protectants like dibenzoyl methane and benzyl benzoate. The usefulness of menthyl benzoate as protectant was found against the harmful effects of wider range of ultraviolet radiation (UVA and UVB). Essentially, in these experiments we adopted a novel, fast, convenient and environmentally compatible screening method not requiring animal and human subject by using the growth and lethality of bacteria exposed to direct and filtered ultraviolet light. The method thus also determined the efficacy of the compound in quantifiable terms on the basis of the survival percentage.

Preparation of the Compounds

Menthyl Benzoate: A solution of 1-menthol (1 gram) in benzoyl chloride (1 ml) was stirred at room temperature for 72 hours. This solution yielded menthyl benzoate of 89.5% purity. Further purification of this product through column chromatography resulted to increase in purity level to at least 98.8%. This fraction yielded colourless crystals and confirmed for purity by $^{1}$HNMR, $^{13}$CNMR, IR and Mass spectra.

Benzyl Benzoate: A mixture of 1 ml benzyl alcohol and 1 ml benzyl chloride was stirred at room temperature for 72 hours. This solution yielded benzyl benzoate of 87.0% purity. Further purification of this product by column chromatography gave at least 99% benzyl benzoate.

Dibenzoyl methane: This commercial chemical was obtained from M/S Lancaster Synthesis Ltd, Eastgate, White Lund, Morecambe, Lancashire LA3 3DY, UK (Catalogue no2104) chemicals with 98% purity level.

UV Protection Assays

UV light is not only harmful to humans but also to all other biological systems including microorganisms. The majority of the studies of the effect of UV light on microbes and its modes of action have shown the formation of thymidine dimers, which cause mutations and excessive exposure thus leads to death of the bacteria. As bacteria are devoid of cellulose or protein wall and are single celled, they are much more sensitive to the UV light and hence efficient bio-indicators of UV damage. Therefore, the assays involving the screening of potential UV protectant compounds against bacterial system exposure in presence and absence of test compound is easy, less time consuming and environmentally safe. We carried out simple experiments involving the bacterium *Escherichia coli* (Wild type) (Kumar, 5. 1976. Journal of Bacteriology, 125: 545–555) as the test system. *Escherichia coli* is a Gram negative bacterium and sensitive to ultraviolet light. The bacterial cells were grown in broth cultures were exposed to UV light for different time periods and the survival in terms of colony forming units was determined to estimate the killing percentage. The experiments comprised of a series of different steps in two distinct manners/routes (Example 1 and 2 below). In these examples, various quantities were mentioned are not confined to the said limits but can be variable depending upon the need and scale of experiment or screen to be employed. Two different approaches as described below were followed. In one case, the bacterial cells were grown in presence of the test compound and then exposed to UV while, in other case the bacteria were exposed to the two wavelength of UV light filtered through a UV transparent film coated with the compound and using uncoated film as control.

EXAMPLE 1

Exposure of the Bacteria to UV Light Through a UV Transparent Film Coated with the Compound Step A: Growing bacterial cultures: The wild type strain, CA 8000 of *Escherichia coli* was used in the assays. A single colony was inoculated in 5 ml Luria broth and incubated at 37° C. temperature for 16 hour in a water bath shaker. Bacteria were grown in presence of test compounds with plain LB as growth medium.

Step B: The bacterial culture was harvested by centrifugation and pellet was suspended in equal amount of sterile distilled water. The bacterial pellet was harvested by centrifuging at 5000 RPM for 10 minute and suspended in 25 ml sterile distilled water.

Step C: About 0.3 ml of the broth culture of the bacteria was transferred to petriplates forming a thin layer at the bottom (in replicates). At least 5 replicates per treatment were used along with control plates containing bacteria.

Step D: The plates were covered with UV transparent film, which was coated with different concentrations of the test compounds. In this invention, we employed market available food wraps (Cling Films) which were found to be 100% transparent.

Step E: In the dark room a UV source was placed at least 10 cm above the plates (which may vary depending upon the experiment). In this invention, the UV torch emitting two-fixed wavelength (312 nm and 365 nm) was used.

Step F: Light source was switched-on for different time intervals for the predetermined lethality levels based on the killing curve of control bacteria determined by UV exposure through uncoated film.

Step G: The viable cfu (colony forming unit) count was determined by serially diluting the exposed and control bacteria and then plating on the Luria agar plates followed by counting the viable units of the bacteria forming colonies (Table 1).

Bacteria were grown in presence of test compounds with plain LB as growth medium.

Step B: Determining killing percentage of bacteria in relation to UV exposure time: This was done in the following steps.

a. The broth culture was diluted to 10 times in sterile water.

b. About 0.3 ml of the diluted bacterial suspension was transferred to the petriplates forming a thin layer at the bottom (in replicates).

c. In the dark room a UV source was placed at least 10 cm above the plates (This distance may vary depending upon the need of the experiment)

TABLE 1

UV protection assay through compound-coated film (50 μg per ml) showing protection provided by menthyl benzoate as protectant at various levels of UV exposure.

| UV exposure equivalent to lethality level (%) | Initial titre (cfu per ml) | Titre after UV exposure (cfu per ml) | | Killing (%) | | Protection (%) |
|---|---|---|---|---|---|---|
| | | Uncoated film | Coated with menthyl benzoate (50 μg per ml) | Uncoated film | Coated with menthyl benzoate (50 μg per ml) | |
| 50 | $2.490 \times 10^8$ | $1.242 \times 10^8$ | $1.400 \times 10^8$ | 50.12 | 43.77 | 12.67 |
| 25 | $2.490 \times 10^8$ | $1.867 \times 10^8$ | $2.020 \times 10^8$ | 25.02 | 18.87 | 24.58 |
| 10 | $2.490 \times 10^8$ | $2.240 \times 10^8$ | $2.415 \times 10^8$ | 10.04 | 3.01 | 70.01 |

In this experiment, out of all the concentrations of the compound menthyl benzoate coated on the film we found 50 μg per ml was the most optimum amount. Increasing the concentration does not increase substantially the level of protection. At all the levels of lethality tested the compound reduced the percentage of lethality of the bacteria. Though the data shown in the example are for UV protection assay at 312 nm but the data of IJV protection at 365 nm were similar and comparable.

EXAMPLE 2

UV Protection Assays for the Bacteria Cultivated in Presence of the Compounds

Step A: Growing bacterial cultures: The wild type strain CA 8000 of *Escherichia coli* was in the assays. A single colony was inoculated in 5 ml Luria broth and incubated at 37° C. temperature for 16 hour in a water bath shaker.

d. The cfu (colony forming unit) count was determined by serially diluting the exposed and control bacteria and plating on the Luria agar plate followed by counting the viable units of the bacteria forming colonies upon incubation at 37° C. overnight.

The dosage for $LD_{70}$ and $LD_{80}$ (LD=lethal dosage) was found to be 120 and 150 seconds UV exposure, respectively in LB grown cells. These two exposure levels were used further in our experiment to test the efficacy of different compounds for UV protection.

Step C: The bacterial cultures were grown in presence of different concentrations of the test compounds, exposed in the same way as in step B and viable cfu count was determined. In these assays it was found that 50 $\mu$g/ml concentration of the compound menthyl benzoate provided a significant protection in comparison to other known UV protactants (Table 2).

TABLE 2

Comparative UV protection activity of benzoate compounds against *Escherichia coli* as assayed by the protocol described above.

| Compounds | Titre estimated (cfu): Initial | Titre estimated (cfu): Final after UV exposure 120 seconds | Titre estimated (cfu): Final after UV exposure 150 seconds | Killing (%) after UV exposure: 120 seconds | Killing (%) after UV exposure: 150 seconds |
|---|---|---|---|---|---|
| Control | $3.73 \times 10^7$ | $1.119 \times 10^7$ | $0.746 \times 10^7$ | 70.00 | 80.00 |
| Dibenzoyl methane | $3.73 \times 10^7$ | $1.162 \times 10^7$ | $1.050 \times 10^7$ | 68.85 | 71.85 |
| Benzyl benzoate | $3.73 \times 10^7$ | $1.460 \times 10^7$ | $1.240 \times 10^7$ | 60.86 | 66.75 |
| Menthyl benzoate | $3.73 \times 10^7$ | $1.660 \times 10^7$ | $1.300 \times 10^7$ | 55.49 | 65.15 |

In this experiment the killing % for the known UV protectants dibenzoyl methane and benzyl benzoate was much less in comparison to the control indicating the level of protection of UV. In terms of protection efficiency these three compounds in a descending series show up as menthyl benzoate>benzoyl benzoate>dibenzoyl methane. It is important to note that menthyl benzoate was better protectant than the commercially used dibenzoyl methane. The procedure is also useful in determining the efficacy of the compounds known for their UV protection described above in this invention.

As the objective of the invention was to find out a new alternative and quick protocol to screen large number of compounds for UV protection, this was achieved by testing the known UV protectants as well as a known compound not used till date for UV protection.

Another preferred objective of the invention was to find out a compound, which can be used for protection to UV light in biological system.

The compound of the invention was found to be safe to the bacterial system as found out in our invention which as such does not kill the bacterial cell and the cfu remain the same for treated and untreated cultures and no decrease of titre was observed by growing the bacteria in presence of the compound.

In this invention, a bacterial model system could be constructed with the simple method to employ in rapid large scale screening of compounds which can protect the cells against UV damage (312 nm to 365 nm) either in form of a sieve or in vicinity of target cells. A variety of compounds including several monoterpenes and their derivatives were screened using Benzyl benzoate and Dibenzoyl methane as control UV screen molecules. The procedure is rapid, novel, most convenient and environmentally compatible not requiring human or animal subject and/or complexities of cell culture in skin testing. Results in this procedure, can be obtained overnight and are 100% interpretable as evident from the control compounds and additionally provide quantifiable data on extent of protection. In this screening approach which itself was the objective of the invention menthyl benzoate was found to provide significant protection with excellent efficiency for both UV radiation (UVA and UVB) and hence making its use as UV protectant evident.

What is claimed is:

1. A formulation comprising menthyl benzoate in an amount between 0.002–0.02% (w/w) formulated in a body care composition used for external UV protection.

2. A method of protecting a biological system against UV radiation comprising the steps of:

obtaining a formulation comprising an effective amount of menthyl benzoate; and applying the formulation to the biological system.

3. The method of claim 2, wherein the menthyl benzoate is present in the formulation in a range of 0.002–0.02% (w/w).

4. The method of claim 2, wherein the formulation is in the form of a body care composition used for external UV protection.

5. The method of claim 2, wherein the biological system is a human.

6. The method of claim 2, wherein the biological system is skin of a human.

* * * * *